(12) United States Patent
Selkee (10) Patent No.: US 8,523,808 B2
(45) Date of Patent: Sep. 3, 2013

(54) MEDICAL DEVICE CONTROL HANDLE WITH INDEPENDENT SELF HOLDING PULLER WIRE ACTUATORS

(75) Inventor: Thomas V. Selkee, Claremont, CA (US)

(73) Assignee: Biosense Webster (Israel), Ltd., Yokneam (IL)

( * ) Notice: Subject to any disclaimer, the term of this patent is extended or adjusted under 35 U.S.C. 154(b) by 0 days.

(21) Appl. No.: 13/299,807

(22) Filed: Nov. 18, 2011

(65) Prior Publication Data
US 2013/0131592 A1  May 23, 2013

(51) Int. Cl.
*A61M 31/00* (2006.01)

(52) U.S. Cl.
USPC .......................... 604/95.04; 604/523; 604/528

(58) Field of Classification Search
CPC ....................................................... A61M 37/00
USPC ...................... 604/95.04, 523, 528
See application file for complete search history.

(56) References Cited

U.S. PATENT DOCUMENTS

| | | | |
|---|---|---|---|
| 5,195,968 A * | 3/1993 | Lundquist et al. | 604/95.04 |
| RE34,502 E | 1/1994 | Webster, Jr. | |
| 5,738,631 A | 4/1998 | Konstorum | |
| 5,891,088 A * | 4/1999 | Thompson et al. | 604/95.04 |
| 6,033,378 A * | 3/2000 | Lundquist et al. | 604/95.01 |
| 6,638,286 B1 * | 10/2003 | Burbank et al. | 606/157 |
| 6,652,506 B2 | 11/2003 | Bowe et al. | |
| 6,673,012 B2 | 1/2004 | Fujii et al. | |
| 7,163,509 B2 | 1/2007 | Abe | |
| 7,285,108 B2 | 10/2007 | Koerner et al. | |
| 7,377,906 B2 | 5/2008 | Selkee | |
| 7,771,416 B2 | 8/2010 | Spivey et al. | |
| 7,846,089 B2 | 12/2010 | Maruyama | |
| 8,048,025 B2 * | 11/2011 | Barenboym et al. | 604/95.04 |
| 2006/0047245 A1 | 3/2006 | Sehra | |
| 2009/0287188 A1 | 11/2009 | Golden et al. | |
| 2010/0004592 A1 * | 1/2010 | Butler | 604/95.04 |
| 2010/0069834 A1 * | 3/2010 | Schultz | 604/95.04 |
| 2011/0054446 A1 | 3/2011 | Schultz | |
| 2013/0018306 A1 * | 1/2013 | Ludwin | 604/95.04 |

FOREIGN PATENT DOCUMENTS

EP      2 289 592 A2     3/2011

OTHER PUBLICATIONS

European Search Report dated Feb. 4, 2013 for European Application No. 12193056.4, 6 pages.

* cited by examiner

*Primary Examiner* — Theodore J Stigell
*Assistant Examiner* — Gerald Landry, II
(74) *Attorney, Agent, or Firm* — Christie, Parker & Hale, LLP (57) ABSTRACT

A medical device control handle has a first actuation member for actuating at least one puller wire in one manipulation of a medical device, including uni-directional deflection, if not a pair of puller wires for bi-directional deflection of a catheter, and a second actuation member for actuating an additional puller wire in another manipulation of the medical device, wherein the first and second actuation members have a common rotational axis without being rotationally coupled. In one embodiment, a first actuation assembly has a first actuator, an arm rotatable about an axis, and a first shaft. The first deflection actuator and the arm are rotationally coupled by the rotation shaft, and the arm has at least one pulley that is engaged with a puller wire. The second wire actuation assembly has a second actuator and a second shaft having a spool portion. Each actuation assembly has a friction-inducing element that provides friction torque between components of each assembly such that the actuators are self-holding.

12 Claims, 11 Drawing Sheets

MEDICAL DEVICE CONTROL HANDLE WITH INDEPENDENT SELF HOLDING PULLER WIRE ACTUATORS

FIELD OF INVENTION

This invention relates to a control handle for medical devices, in particular, a control handle having multiple mechanisms controlling multiple puller wires.

BACKGROUND

Electrode catheters have been in common use in medical practice for many years. They are used to stimulate and map electrical activity in the heart and to ablate sites of aberrant electrical activity. Atrial fibrillation is a common sustained cardiac arrhythmia and a major cause of stroke. This condition is perpetuated by reentrant wavelets propagating in an abnormal atrial-tissue substrate. Various approaches have been developed to interrupt wavelets, including surgical or catheter-mediated atriotomy. Prior to treating the condition, one has to first determine the location of the wavelets. Various techniques have been proposed for making such a determination, including the use of catheters with a mapping assembly that is adapted to measure activity within a pulmonary vein, coronary sinus or other tubular structure about the inner circumference of the structure. One such mapping assembly has a tubular structure comprising a generally circular main region generally transverse and distal to the catheter body and having an outer circumference and a generally straight distal region distal to the main region. The tubular structure comprises a non-conductive cover over at least the main region of the mapping assembly. A support member having shape-memory is disposed within at least the main region of the mapping assembly. A plurality of electrode pairs, each comprising two ring electrodes, are carried by the generally circular main region of the mapping assembly.

In use, the electrode catheter is inserted into a guiding sheath which has been positioned a major vein or artery, e.g., femoral artery, and guided into a chamber of the heart. Within the chamber, the catheter is extended past a distal end of the guiding sheath to expose the mapping assembly. The catheter is maneuvered through movements that include deflection of a distal portion of the catheter so that the mapping assembly is positioned at the tubular region in the heart chamber. The ability to control the exact position and orientation of the catheter and also the configuration of the mapping assembly is critical and largely determines how useful the catheter is.

Steerable catheters are generally well-known. For example, U.S. Pat. No. Re 34,502 describes a catheter having a control handle comprising a housing having a piston chamber at its distal end. A piston is mounted in the piston chamber and is afforded lengthwise movement. The proximal end of the elongated catheter body is attached to the piston. A puller wire is attached to the housing and extends through the piston, through the catheter body, and into a tip section at the distal end of the catheter body. The distal end of the puller wire is anchored in the tip section of the catheter. In this arrangement, lengthwise movement of the piston relative to the housing results in deflection of the catheter tip section.

The design described in U.S. Pat. No. RE 34,502 is generally limited to a catheter having a single puller wire. If bi-directional deflection is desire, more than one puller wire becomes necessary. Moreover, if more control is desired, such as contraction of the mapping assembly, an additional puller wire is needed. Furthermore, it is desirable that the mechanism for actuating the additional puller wire be self-holding such that the mechanism can maintain the contraction of the mapping assembly without the need for continuous control by the user. Accordingly, a need exists for a control handle capable of moving a third puller wire that can be used in a hands-free manner.

SUMMARY OF THE INVENTION

The present invention is directed to a medical device control handle. As medical devices, especially, electrophysiology catheters, become more complex with more components to actuate, a control handle should provide independent control of multiple puller wires. The control handle of the present invention utilizes a first actuation member for actuating at least one puller wire in one manipulation of a medical device, including uni-directional deflection, if not a pair of puller wires for bi-directional deflection of a catheter, and a second actuation member for actuating an additional puller wire in another manipulation of the medical device, wherein the first and second actuation members have a common rotational axis without being rotationally coupled.

In one embodiment, a control handle for a medical device with one puller wire for manipulating one feature, and another puller wire for manipulating another feature, has a first actuation assembly and a second actuation assembly. The first actuation assembly has a first actuator, an arm rotatable about an axis, and a first shaft. The first deflection actuator and the arm are rotationally coupled by the rotation shaft, and the arm has at least one pulley that is engaged with a puller wire. The second wire actuation assembly has a second actuator and a second shaft having a spool portion. User rotation of the first actuator rotates the arm in moving the pulley to draw the first puller wire which manipulates the first feature of the medical device whereas user rotation of the second actuator wraps the second puller wire on the spool member which manipulates the second feature of the medical device. Even though the first actuation assembly and the second actuation assembly are axially aligned and have a common rotational axis which simplifies design of the control handle and saves space in the control handle, the shafts of each actuation assembly are rotationally independent of each other such that each actuation assembly operates independently of the other and that actuation of a puller wire of one assembly is independent of actuation of a puller wire of the other assembly.

In a more detailed embodiment, each actuation assembly has a friction-inducing element that provides friction torque between components of each assembly such that the actuators are self-holding. This feature allows hands-free operation of the control handle wherein the user need not actively hold an actuator in order to maintain the manipulation of the respective feature of the medical device.

BRIEF DESCRIPTION OF THE DRAWINGS

These and other features and advantages of the present invention will be better understood by reference to the following detailed description when considered in conjunction with the accompanying drawings. It is understood that selected structures and features have not been shown in certain drawings so as to provide better viewing of the remaining structures and features.

DETAILED DESCRIPTION OF THE INVENTION

Figure 1:
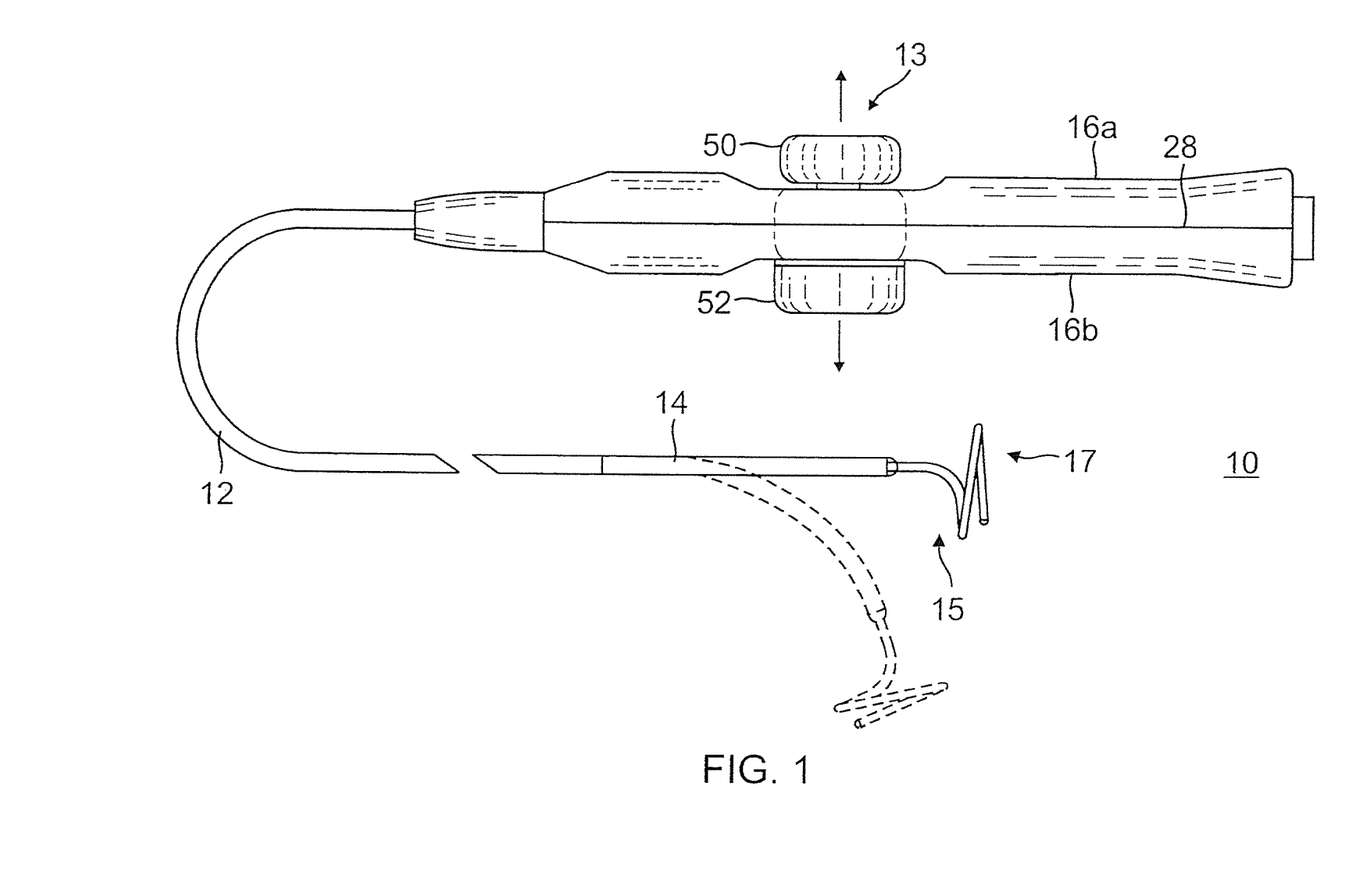
FIG. 1 is a top plan view of one embodiment of the catheter of the present invention.

The present invention is directed to a control handle 10 for use with a medical device with at least two tensile members, e.g., puller wires or the like, for actuating at least two independent movements or manipulations of components of the medical device. The control handle may be used with any variety of medical devices, for example, an electrophysiology (EP) catheter 10 configured for mapping and/or ablation of tissue, including the heart, an embodiment of which is illustrated in FIG. 1. Advantageously, a first actuator is used to manipulate a feature of the medical device and a second actuator is used to manipulate another feature of the medical device.

The catheter 10 of FIG. 1 comprises an elongated catheter body 12, a deflectable intermediate section 14 at a distal end of the catheter body 12, and a tip section 15 including a distal assembly 17 having, for example, a helical form, at a distal end of the intermediate section 14. In the illustrated embodiment of FIGS. 1 and 6, a control handle 16 for use with the catheter has a first actuator, e.g., bi-directional deflection knob 50, that is configured to actuate at least one puller wire, if not a pair of puller wires, extending from the control handle 16 and through the catheter body 12 and intermediate section 14 for uni- or bi-directional deflection of the intermediate section. In accordance with a feature of the present invention, the control handle has a second actuator, e.g., a dial 52, opposing the first actuator 50, for actuating yet another (or third) puller wire for independent manipulation or adjustment of a distal assembly 17 extending from the intermediate section 14, for example, to contract the helical form of the distal assembly. Each actuator can be operated separately and independently without affecting the other actuator or its puller wire.

Figure 2A:
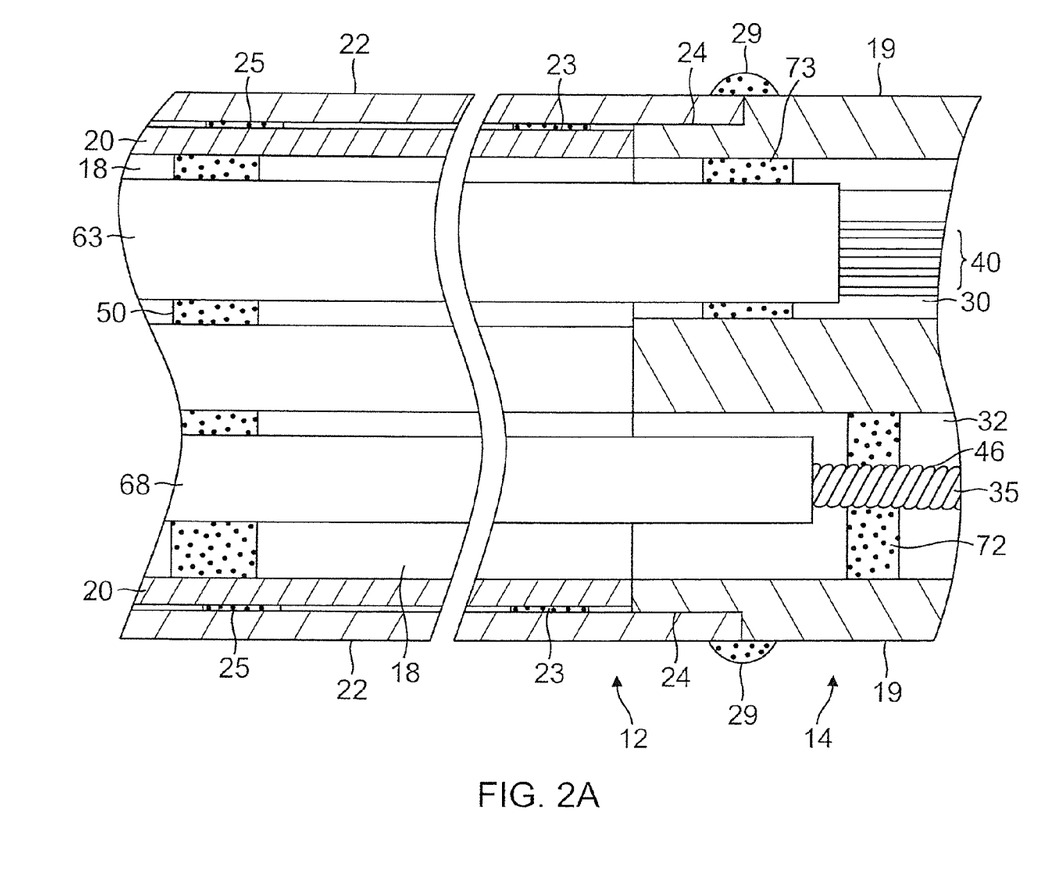
FIG. 2A is a side cross-sectional view of an embodiment of a junction of a catheter body and an intermediate section, taken along a first diameter.
Figure 2B:
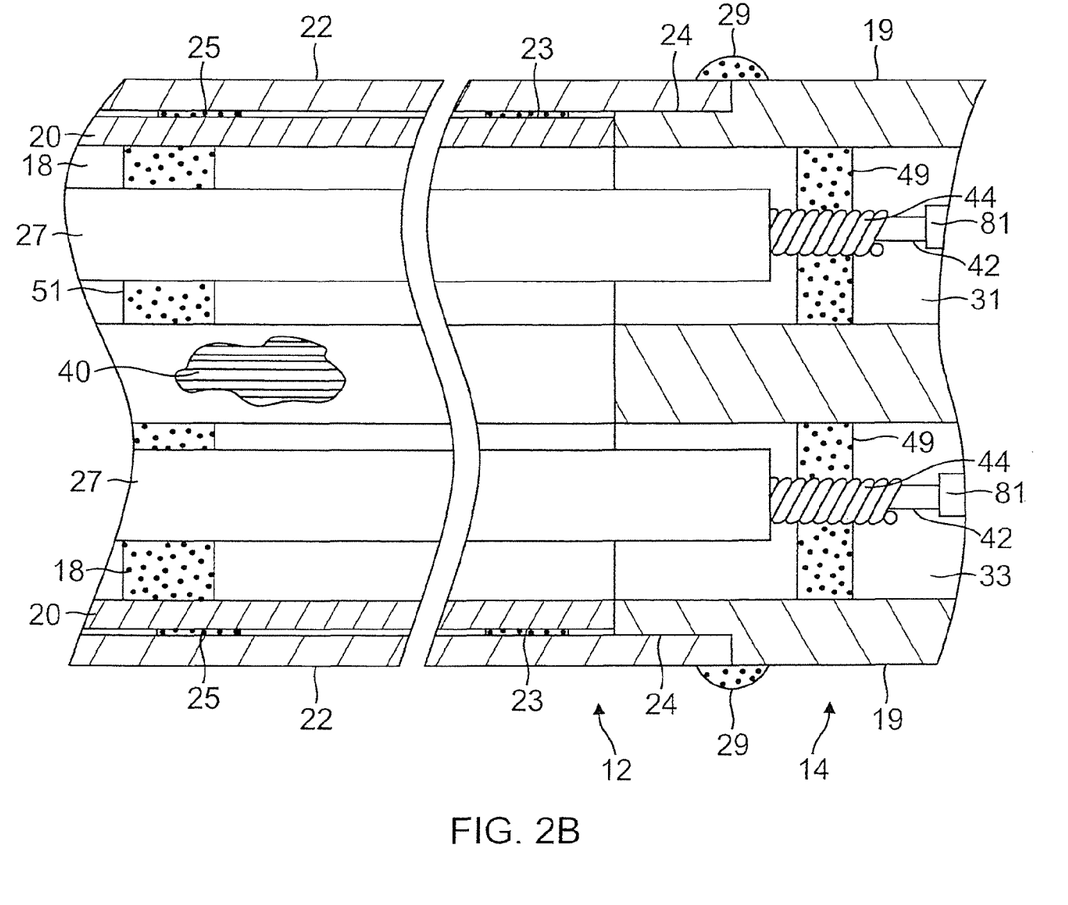
FIG. 2B is a side cross-sectional view of the embodiment of the junction of FIG. 2A, taken along a second diameter generally perpendicular to the first diameter.

With reference to FIGS. 2A and 2B, the catheter body 12 comprises a single, central or axial lumen 18. The catheter body 12 is flexible, i.e., bendable, but substantially non-compressible along its length. The catheter body 12 may be of any suitable construction and made of any suitable material. In one embodiment, the catheter body 12 comprises an outer wall 22 made of a polyurethane or PEBAX. The outer wall 22 comprises an imbedded braided mesh of stainless steel or the like to increase torsional stiffness of the catheter body 12 so that, when the control handle 16 is rotated, the tip section of the catheter 10 will rotate in a corresponding manner.

The outer diameter of the catheter body 12 is not critical, but is preferably no more than about 8 French. Likewise the thickness of the outer wall 22 is not critical. The inner surface of the outer wall 22 is lined with a stiffening tube 20, which can be made of any suitable material, preferably polyimide. The stiffening tube 20 is held in place relative to the outer wall 22 at the proximal end of the catheter body 12. A first glue joint 23 is made between the distal ends of the stiffening tube 20 and the outer wall 22 by a fast drying glue, e.g. Super Glue®. Thereafter, a second glue joint 25 is formed between the proximal ends of the stiffening tube 20 and outer wall 22 using a slower drying but stronger glue, e.g., polyurethane.

The stiffening tube 20, along with the braided outer wall 22, provides improved torsional stability while at the same time minimizing the wall thickness of the catheter, thus maximizing the diameter of the single lumen. The outer diameter of the stiffening tube 20 is about the same as or slightly smaller than the inner diameter of the outer wall 22. Polyimide tubing is suitable because it may be very thin walled while still providing very good stiffness. This maximizes the diameter of the central lumen 18 without sacrificing strength and stiffness. Polyimide material is typically not used for stiffening tubes because of its tendency to kink when bent. However, it has been found that, in combination with an outer wall 22 of polyurethane, PEBAX or other similar material, particularly having a stainless steel braided mesh, the tendency for the polyimide stiffening tube 20 to kink when bent is essentially eliminated with respect to the applications for which the catheter is used.

In one embodiment, the outer wall 22 has an outer diameter of about 0.092 inch and an inner diameter of about 0.063 inch and the polyimide stiffening tube 20 has an outer diameter of about 0.0615 inch and an inner diameter of about 0.052 inch.

Figure 3:
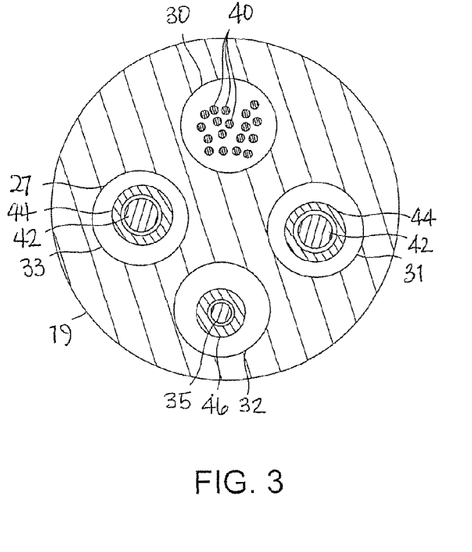
FIG. 3 is an end cross-sectional view of the intermediate section of FIGS. 2A and 2B.

As shown in FIGS. 2A, 2B and 3, the intermediate section 14 comprises a shorter section of tubing 19 with multiple lumens, for example, first, second, third and fourth lumens 30, 31, 32 and 33. The tubing 19 is made of a suitable non-toxic material which is preferably more flexible than the catheter body 12. A suitable material for the tubing 19 is braided polyurethane, i.e., polyurethane with an embedded mesh of braided stainless steel or the like. The outer diameter of the intermediate section 14, like that of the catheter body 12, is preferably no greater than about 8 French. The size of the lumens is not critical. In one embodiment, the intermediate section has an outer diameter of about 7 French (0.092 inch) and the lumens are generally about the same size, having a diameter of about 0.022 inch, or selected lumens can have a slightly larger diameter of about 0.036 inch.

A means for attaching the catheter body 12 to the intermediate section 14 is illustrated in FIGS. 2A and 2B. The proximal end of the intermediate section 14 comprises an inner counter bore 24 that receives the outer surface of the polyimide stiffener 20. The intermediate section 14 and catheter body 12 are attached by glue 29 or the like.

As shown in FIGS. 2A and 2B, extending through the single lumen 18 of the catheter body 12 are various components, for example, lead wires and multiple puller wires, and any other wires or cables. Longitudinal movement of the puller wires relative to the catheter body 12 enables user control of various parts of the catheter via the control handle. As mentioned, in one embodiment, there are first and second deflection puller wires 42 for deflecting the intermediate section 14 and a third puller wire 35 for manipulating and adjusting the distal assembly 17 of the tip section 15.

A single lumen catheter body 12 may be preferred over a multi-lumen body because the single lumen 18 body can permit better tip control when rotating the catheter 10. The single lumen 18 permits the components passing therethrough to float freely within the catheter body. If such components were restricted within multiple lumens, they can build up energy when the handle 16 is rotated, resulting in the catheter body 12 having a tendency to rotate back if, for example, the handle is released, or if bent around a curve, to flip over, either for which are undesirable performance characteristics.

As also shown in FIG. 3, one deflection puller wire 42 extends through the central lumen 18 of the catheter body 12 and into the second lumen 31 of the intermediate section 14. Another deflection puller wire 42 extends through the central lumen 18 and into the fourth lumen 33 of the intermediate section 14. In that regard, the lumens 31, 33 should be off-axis and diametrically opposed to each other for bi-directional deflection in a plane. The distal ends of the deflection puller wires 42 are anchored to the wall of the tubing 19 near the distal end of the intermediate section 14 by means of T-anchors (not shown) as understood by one of ordinary skill in the art. In the intermediate section 14, each deflection puller wires 42 extends through a plastic, e.g. Teflon®, sheath 81, which prevents the deflection puller wires 42 from cutting into the wall of the tubing 19 of the intermediate section 14 when the intermediate section 14 is deflected.

As shown in FIG. 2B, compression coils 44 in surrounding relation to the deflection puller wires 42 extend from the proximal end of the catheter body 12 to the proximal end of the intermediate section 14. The compression coils 44 are made of any suitable metal, e.g., stainless steel. The compression coils 44 are tightly wound on itself to provide flexibility, i.e., bending, but to resist compression. The inner diameter of the compression coils 44 is preferably slightly larger than the diameter of the puller wires 42. For example, when a puller wire 42 has a diameter of about 0.007 inches, the compression coil 44 preferably has an inner diameter of about 0.008 inches. The Teflon® coating on the puller wire 42 allows them to slide freely within the compression coils 44. The outer surface of the compression coils 44 is covered by a flexible, non-conductive sheath 27 to prevent contact between the compression coils 44 and other components, such as lead wires and cables, etc. In one embodiment, a non-conductive sheath is made of polyimide tubing.

The compression coils 44 are anchored at their proximal ends to the proximal end of the stiffening tube 20 in the catheter body 12 by glue joint 51 (FIG. 2B) and at its distal end near the proximal end of the intermediate section 14 in the second lumen 31 and fourth lumen 33 by glue joints 49 (FIG. 2B).

Figure 4:
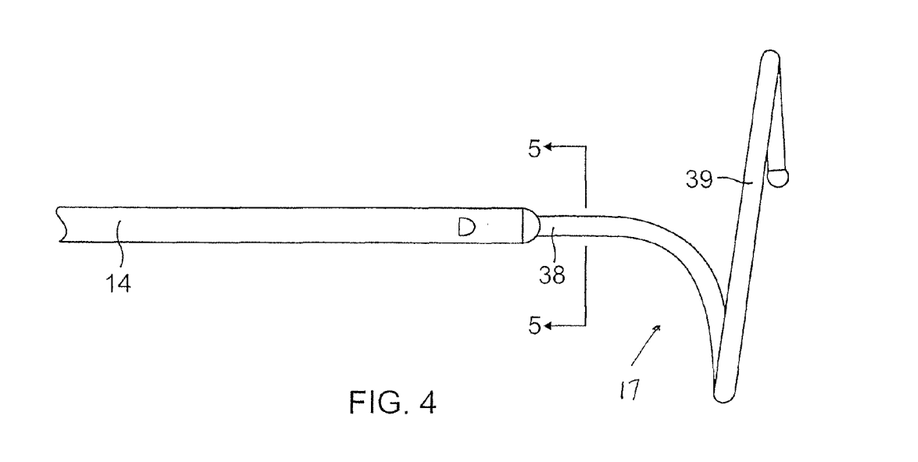
FIG. 4 is a side view of an embodiment of a distal assembly.
Figure 5:
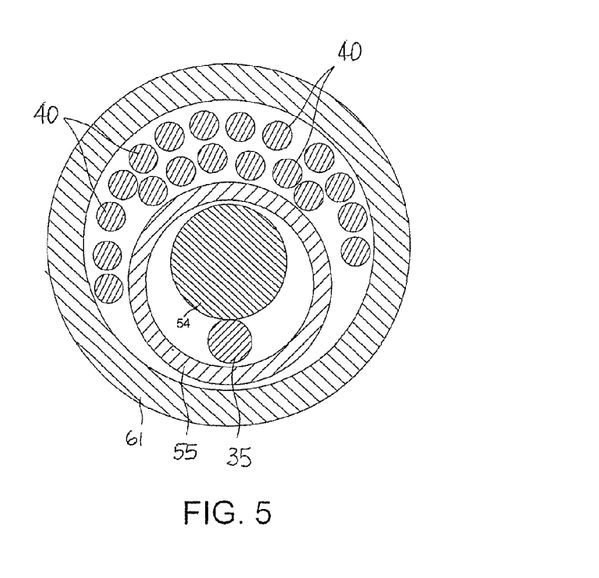
FIG. 5 is an end cross-sectional view of a generally straight proximal portion of the distal assembly of FIG. 4, taken along line 5-5.

With reference to FIG. 4, at the distal end of the intermediate section 14 is the distal assembly 17. The distal assembly 17 comprises a generally straight proximal region 38 and a generally circular main region 39. The proximal region 38 is mounted on the intermediate section 14 and the generally circular main region carries a plurality of electrodes for mapping and/or ablation. In the embodiment of FIG. 5, the distal assembly includes a tubing 61. A shape memory member 54 and lead wires 40 for electrodes carried on the distal assembly extend through the lumen of the tubing 61 and into the intermediate section 14 and the catheter body 12.

In the disclosed embodiment, the third or contraction puller wire 35 is provided to contract the generally circular main region 39 to thereby change or reduce its diameter, for example, when mapping or ablating circular or tubular regions of the heart. The contraction wire 35 has a proximal end anchored in the control handle 16 as described further below. The contraction wire 35 extends through the central lumen 18 of the catheter body 12, through the third lumen 32 of the intermediate section 14 (FIG. 3) and into the distal assembly 17 (FIG. 5).

A third compression coil 46 is situated within the catheter body 12 and intermediate section shaft 14 in surrounding relation to the contraction wire 35 (FIG. 2A). The third compression coil 46 extends from the proximal end of the catheter body 12 and to near the distal end of the third lumen 32 of the intermediate section 14. The third compression coil 46 is made of any suitable metal, such as stainless steel, and is tightly wound on itself to provide flexibility, i.e., bending, but to resist compression. The inner diameter of the third compression coil 46 is preferably slightly larger than the diameter of the contraction wire 35. The outer surface of the compression coil 46 is covered by a flexible, non-conductive sheath 68, e.g., made of polyimide tubing. The third compression coil 46 preferably is formed of a wire having a square or rectangular cross-sectional area, which makes it less compressible than a compression coil formed from a wire having a circular cross-sectional area. As a result, the third compression coil 46 keeps the catheter body 12, and particularly the intermediate section 14, from deflecting when the contraction wire 35 is manipulated to contract the distal assembly 17 as it absorbs more of the compression.

The third compression coil 46 is anchored at its proximal end to the stiffening tube 20 of the catheter body 12 by the proximal glue joint 50 and to the intermediate section 14 by a distal glue joint.

It is understood that glue joints throughout the catheter 10 may comprise polyurethane glue or the like. The glue may be applied by means of a syringe or the like through a hole made in the tubing walls. Such a hole may be formed, for example, by a needle or the like that punctures the tubing walls where the needle is heated sufficiently to form a permanent hole. The glue is then introduced through the hole to wick around the component(s) within the tubing to form a glue joint about the entire circumference of the component(s).

The lead wires 40 attached to the ring electrodes on the distal assembly 17 extend through the first lumen 30 of the intermediate section 14 (FIG. 2A), through the central lumen 18 of the catheter body 12, through the control handle 16, and terminate at their proximal end in a connector (not shown) which is connected to an appropriate monitor or other device for receiving and displaying the information received from the ring electrodes. The portion of the lead wires 40 extending through the central lumen 18 of the catheter body 12, control handle 16 and proximal end of the intermediate section 14 is enclosed within a protective sheath 63, which can be made of any suitable material, preferably polyimide.

An electromagnetic position sensor (not shown) is mounted in or near the distal assembly 17, e.g., in the distal end of the intermediate section 14. A sensor cable 36 extends from the sensor into the lumen 30 of the intermediate section (along with the electrode lead wires 40), into the central lumen 18 of the catheter body 12 and into the control handle where it terminates in a suitable connector (not shown).

Figure 6:
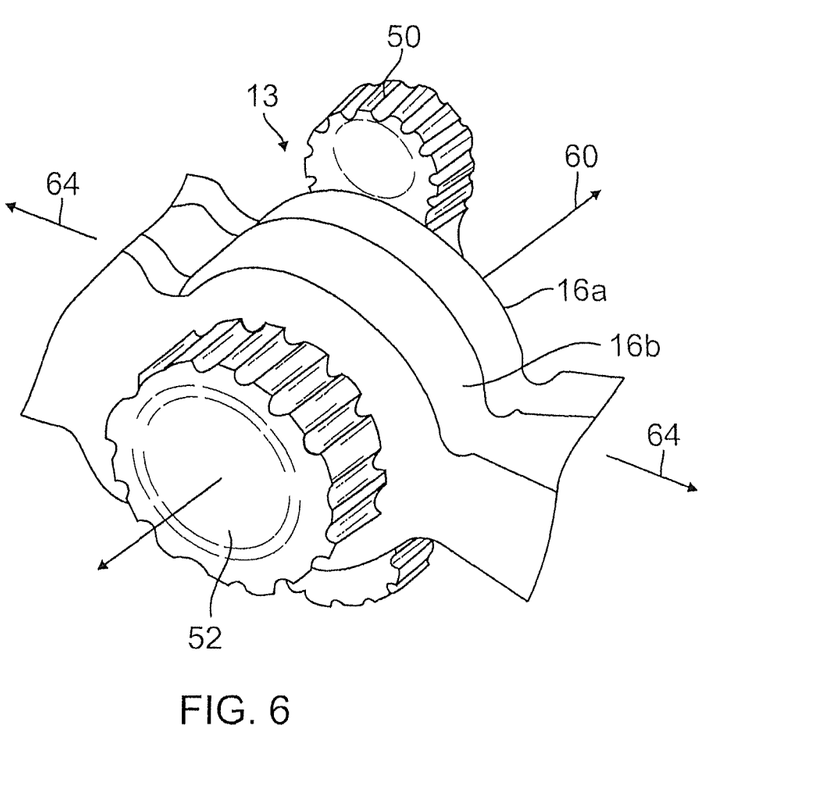
FIG. 6 is a partial view of the control handle of FIG. 1, showing a knob and a dial.
Figure 7:
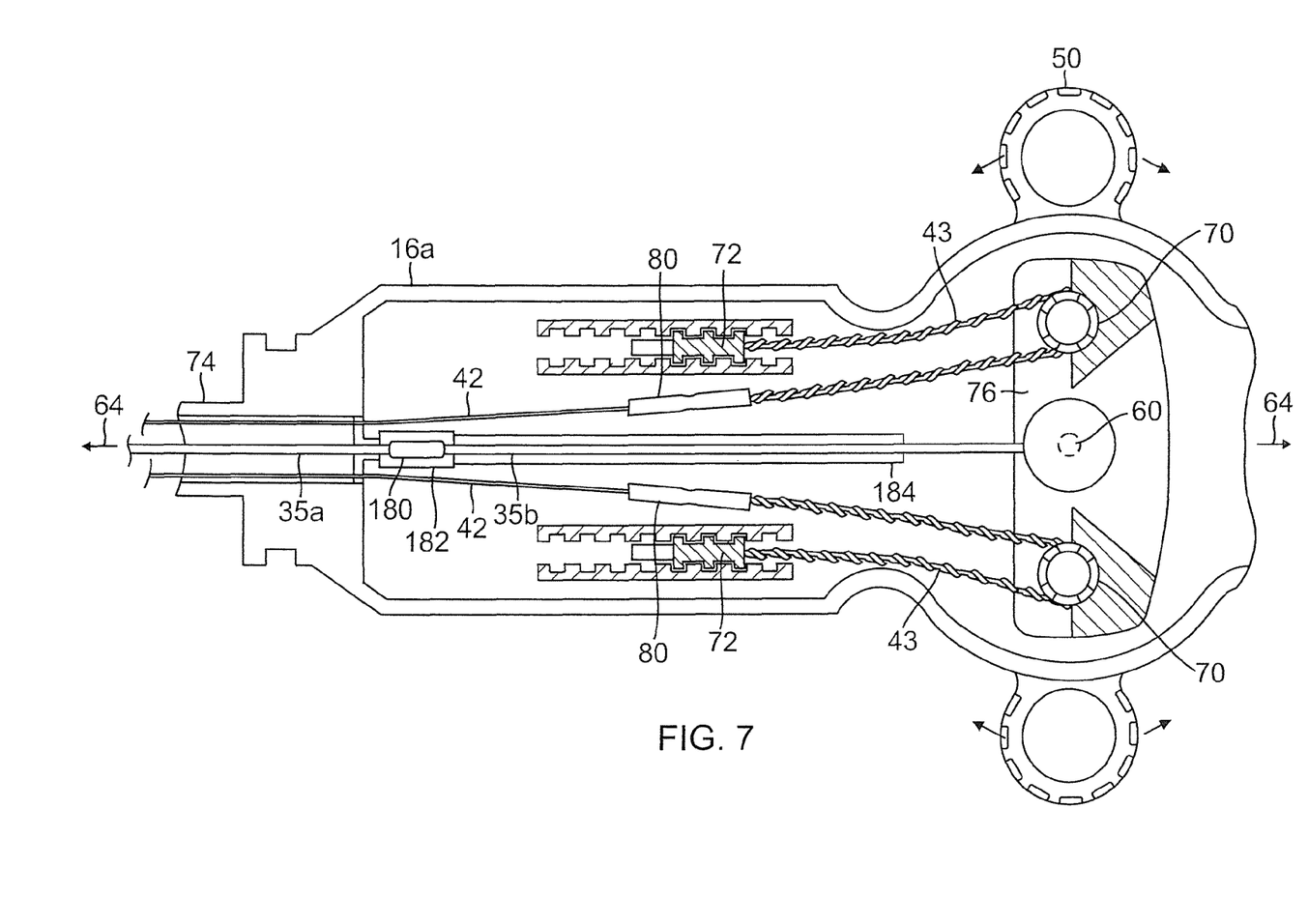
FIG. 7 is a top plan view of an embodiment of a control handle housing half.

In the illustrated embodiment of FIGS. 6 and 7, the control handle 16 includes components of a steering or deflection control assembly 13 that includes the deflection knob 50 for bi-directional deflection of the intermediate section 14 via the pair of puller wires 42. Each puller wire 42 is made of any suitable metal, such as stainless steel or Nitinol. Preferably each puller wire has a low friction coating, such as a coating of Teflon® or the like. Each puller wire has a diameter preferably ranging from about 0.006 inch to about 0.012 inch. Preferably both of the puller wires have the same diameter. Flat puller wires may be used in place of round puller wires. Their cross sectional dimensions should be such that they provide comparable tensile strengths as round puller wires.

Alternatively, the puller wires may be replaced in its entirety or in part by tensile fibers. The fibers may be of a high modulus fiber material, preferably having an ultimate tensile strength substantially in the range of 412-463 ksi (2480-3200 Mpa) such as High Molecular Density Polyethylene (e.g., Spectra™ or Dyneema™), a spun para-aramid fiber polymer (e.g., Kevlar™) or a melt spun liquid crystal polymer fiber rope (e.g., Vectran™), or a high strength ceramic fiber (e.g., Nextel™). The term fiber is used herein interchangeably with the term fibers in that the tensile fiber may be of a woven or braided construction. In any case, these materials tend to be flexible, providing suitable durability when used in wrapped engagement with the pulleys and the like for greater throw in deflecting the catheter tip. Further, they are substantially non-stretching, which increases the responsiveness to the manipulation of the control handle, and nonmagnetic so that they generally appear transparent to an MRI. The low density of the material causes it to be generally transparent to an x-ray machine. The materials can also be nonconductive to avoid shorting. Vectran™, for example, has high strength, high abrasion resistance, is an electrical insulator, nonmagnetic, is polymeric, and has low elongation under sustained loading conditions. It is therefore understood that the term "wire" as used herein may be a wire, a tensile fiber, or a tensile member comprising wire segment(s) and tensile fiber segment(s).

A suitable deflection assembly with a deflection dial and tension adjustment is described in U.S. Pat. No. 7,377,906, the entire disclosure of which is hereby incorporated by reference. For the present invention, reference is made to illustrated embodiment of FIGS. 1, 6 and 7. The control handle 16 comprises a generally elongated handle housing, which can be made of any suitable rigid material. The housing can be of a unitary construction or of two opposing halves 16a, 16b that are joined by glue, sonic welding or other suitable means. The steering assembly 13 provides bi-directional deflection of the intermediate section 14 in response to manipulations of the knob 50 by a user. The steering assembly defines a generally central rotational axis 60 in relation to its components. The axis 60 is generally perpendicular to a longitudinal axis 64 of the control handle.

Figure 9:
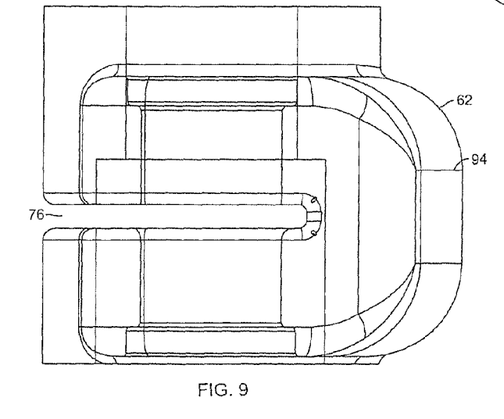
FIG. 9 is a side view of an embodiment of a pulley arm.
Figure 10:
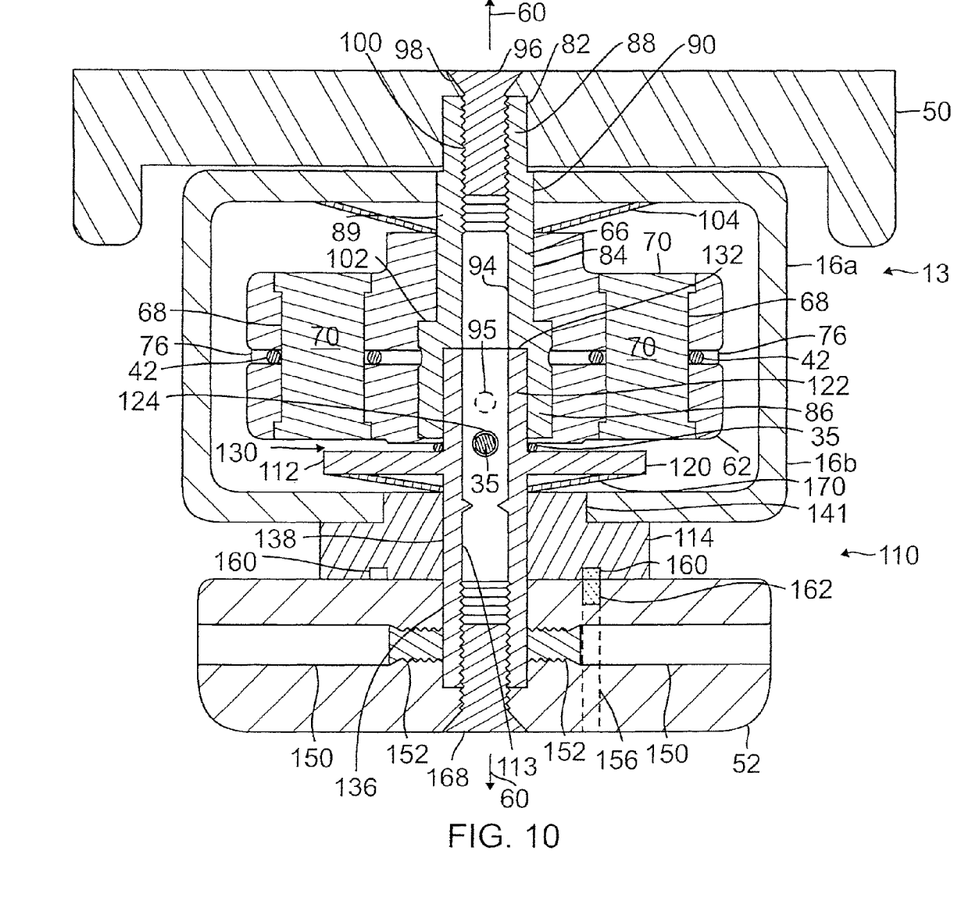
FIG. 10 is an end cross sectional view of the control handle of FIG. 1.
Figure 11:
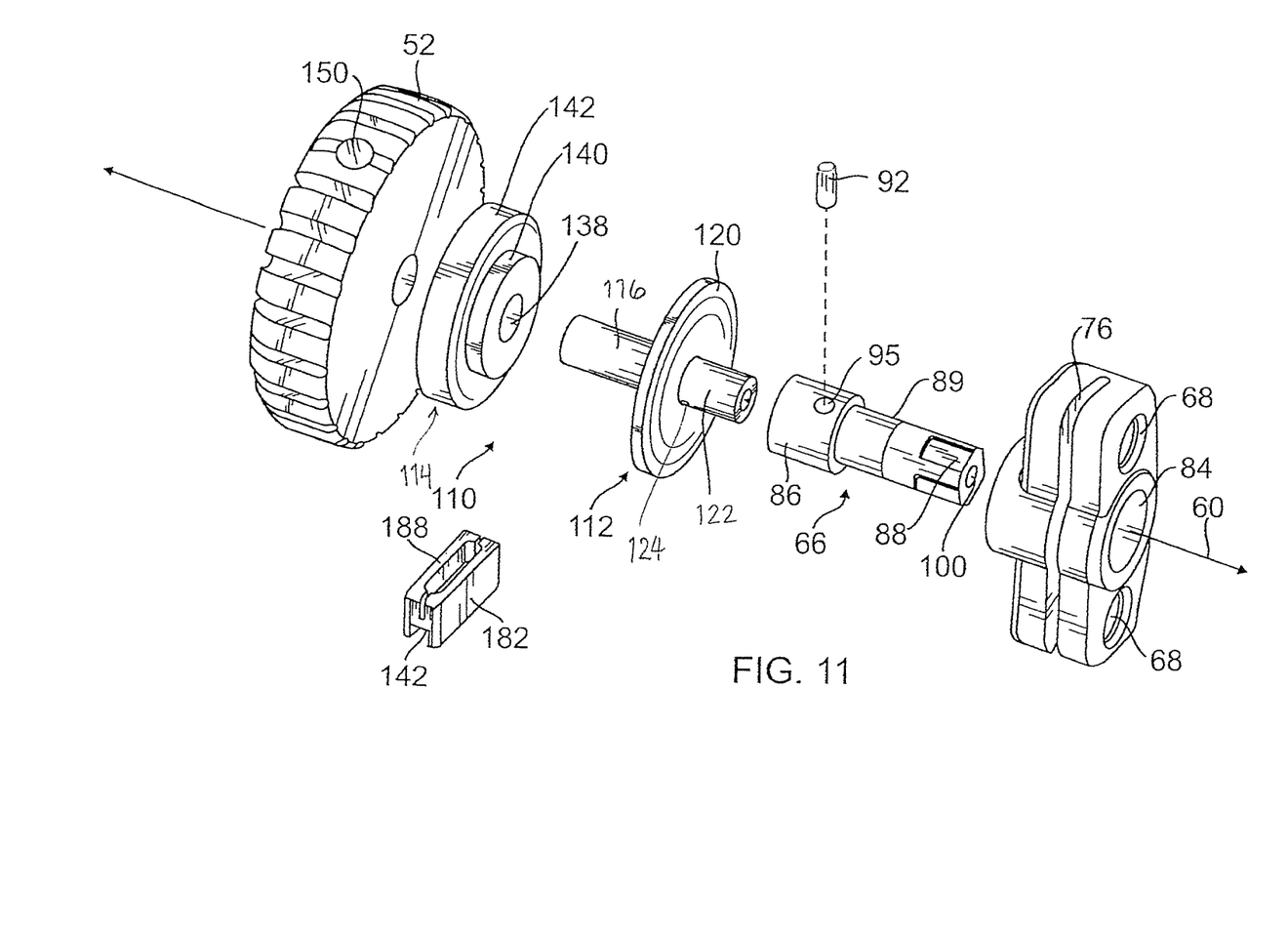
FIG. 11 is an exploded perspective view of embodiments of a steering assembly and of an independent puller wire actuation assembly.
Figure 16:
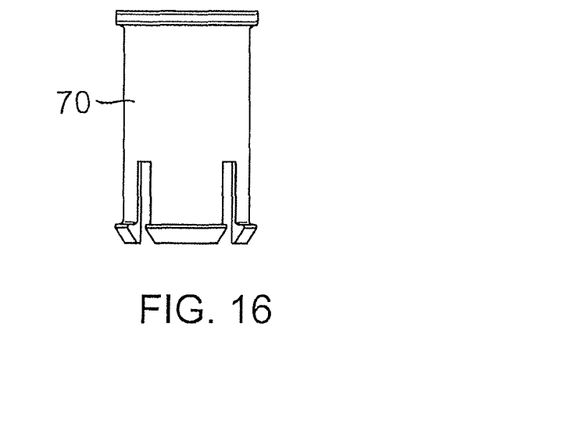
FIG. 16 is a side view of an embodiment of a pulley.

With reference to FIGS. 10 and 11, the steering assembly 13 includes the first control knob 50, a rotatable pulley arm 62 and a first actuator shaft 66. The shaft has a smaller end 88, a mid-section 89, a larger female end 86, and a longitudinal bore 100 extending the length of the shaft. The length of the shaft 66 is greater than a thickness of the arm 62 so that only the mid-section 89 and the larger female end 86 extend through a central bore 84 of the arm 62 while the smaller end 88 protrudes from the arm. The arm has two apertures 68 that oppose each other from across the shaft 66. Each aperture houses a pulley 70 (FIG. 16) that engages with and acts on a respective puller wire 42 that is wrapped or wound on the pulley. The arm 62 and the shaft 66 are rotatably coupled by a press-fit connection pin 92 that extends transversely through aligned hole 94 formed in the atm 62 (FIG. 9) and hole 95 (FIG. 11) formed in the larger female end 86. Notably, the pin does not protrude into the bore 100 of the shaft 66.

Figures 8A, 8B:
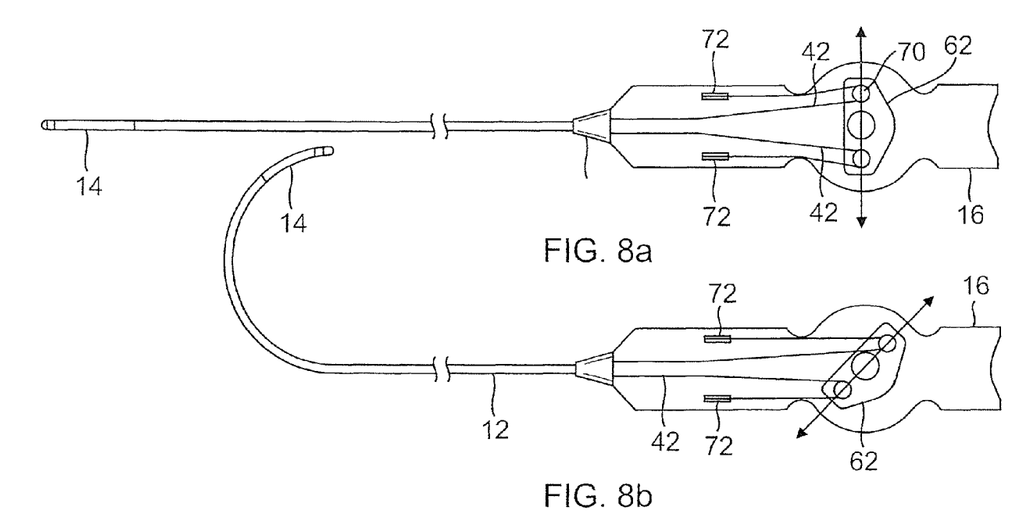
FIG. 8A-8C are schematic diagrams of the control handle housing half of FIG. 7 in a neutral configuration, a right deflection configuration, and a left deflection configuration.
Figure 8C:
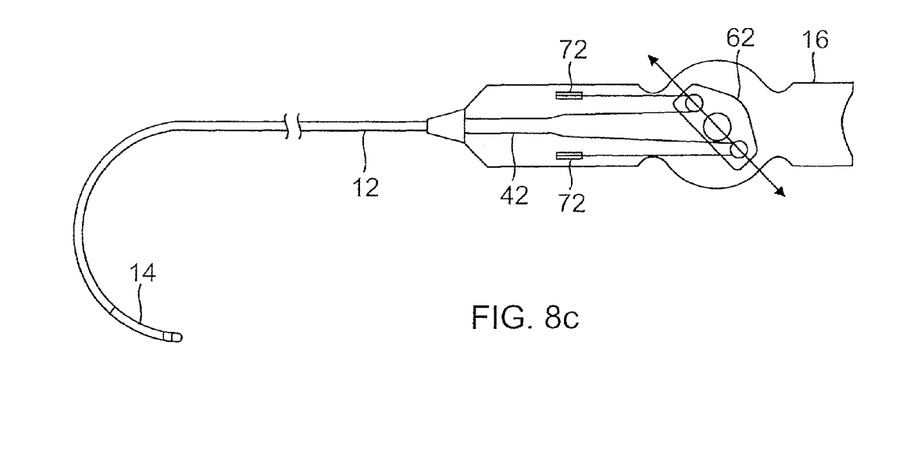

The smaller end 88 of the shaft 66 is inserted through a through hole 90 formed in the housing half 16a and received in a central bore 82 of the knob 50. The knob 50 and the end 88 are rotatably coupled by an interlocking polygonal cross-section configuration, such as a square, hexagonal or octagonal shape. As such, to deflect the catheter, the knob 50 is rotated in one direction, which rotates the shaft 66 and the arm in the same direction. As shown in FIGS. 8a-8c, the pulley 70 in the direction of rotation of the knob 50 draws on its puller wire 42 deflecting the intermediate section 14 in that direction while the opposite pulley 70 releases its puller wire 42. Such coordinated draw and release action on the puller wire pair accomplishes deflection of the intermediate section 14.

Referring to FIGS. 7 and 9, the pair of puller wires 42 enter the control handle 16 via a port 74 in the distal end of the control handle. The puller wires enter the arm 62 through a slit opening 76 thinned in the arm (FIG. 9) and each is wrapped or wound about a respective pulley 70 about 180 degrees before exiting the arm through the slit opening 76.

Because of the repeated cycles of bending each puller wire can experience around its pulley, the segment of each puller wire within the control handle, and especially around the pulleys, may comprise a tensile fiber segment such as described hereinabove, which can better withstand stress and strain. To that end, a crimped connector 80 is provided to connect a proximal end of each first and second puller wire segments 42a to a distal end of a respective tensile fiber segment 42b.

Best seen in FIG. 10, a first locking cap screw 96 is inserted through an opening 98 leading to the through-bore 82 of the deflection knob 50 and received in the longitudinal bore 100 of the first shaft 66. The locking flat head cap screw 96 secures the knob 50 to the shaft 66. The shaft 66 in turn secures the arm 62 and housing half 16a to each other. At a junction between the mid-section 89 and the larger circumferential female end 86 of the shaft 66, a shoulder 102 abuts with a smaller inner diameter of the through-bore 84 of the arm 62. As such, the female end portion 86 is pulled against the arm 62 when the locking cap screw 96 is tightened against the knob 50. In this manner, the components of the deflection assembly 13, including the arm 62, the shaft 66, the knob 50 and locking cap screw 96, are housed generally in the interior of the housing half 16a.

Figure 12:
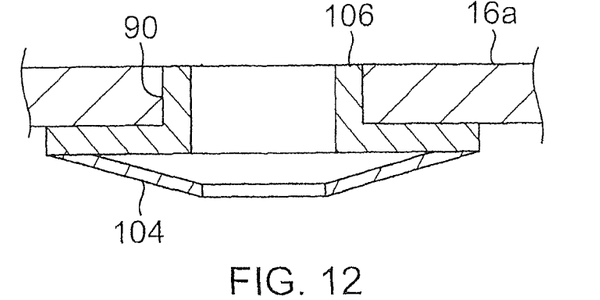
FIG. 12 is a partial side cross-sectional view of an alternate embodiment of control handle housing half.

The bi-directional steering assembly 13 also includes a friction-inducing element, including a washer 104, e.g., a Belleville washer, to render the deflection knob 50 self-holding. In the illustrated embodiment of FIG. 10, the washer 104 is positioned on the shaft 66 between the handle housing 16a and the arm 62. The washer is compression preloaded under the locking cap screw 96 and provides friction torque with the contacting surfaces of the housing half 16a and the arm 62 to hold the knob 50 in the rotational position set by the user thus holding the deflection of the intermediate section 14. To that end, the housing half can be constructed of a plastic material with fiberglass, for example, approximately 30% fiberglass by volume, to minimize risk of permanent deformation under long term loading conditions when the washer is compressed. An alternate embodiment is illustrated in FIG. 12, where a sintered metal sleeve bearing 106 circumferentially lines the through-hole 90 of the housing handle 16a (e.g., by insert molding) to prevent permanent deformation or "creep" of the handle housing under long term compression loading.

Figure 13:
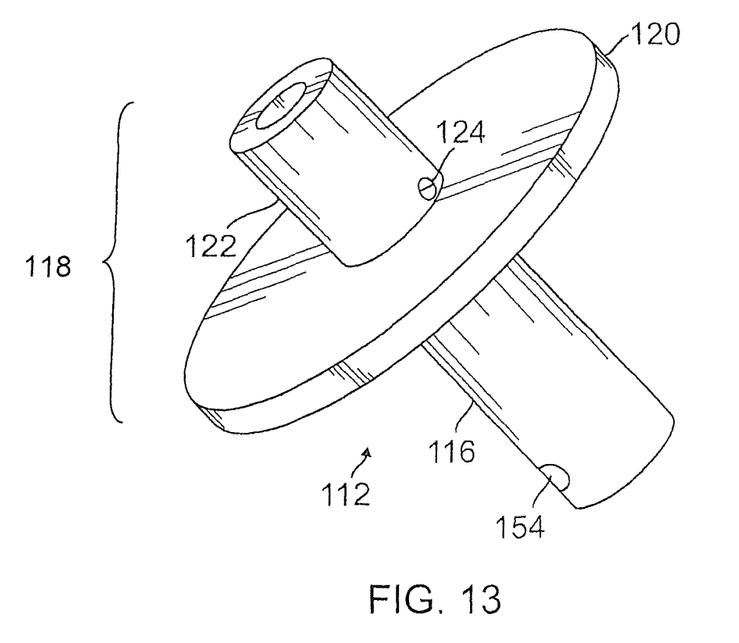
FIG. 13 is a perspective view of an embodiment of a shaft of the actuation assembly.

Housed generally in the other housing half 16b is a second independent puller wire actuation assembly 110 which includes a second shaft 112, a bearing 114 and the actuation dial 52. Providing friction adjustment in the actuation of the third puller wire dial 52, the shaft 112 as illustrated in FIG. 13, includes an elongated shaft body 116, a spool portion 118 at one end having a rim 120 and a drum 122 on which a proximal portion of a third puller or contraction wire 35 is wound, and anchored, for example, by means of a knot tied through a through hole 124 extending transversely through the shaft body. A majority of the drum is received in the through-bore 100 of the first shaft 66 at the larger female end portion 86 so that the first and second shafts 66 and 112 are axially aligned. A predetermined depth of a neck formation 132 in the bore 100 of the first shaft 66 provides a gap 130 between the arm 62 and the rim 120 so that a narrow band of the drum is exposed in the gap 130 for the third puller wire 35 to be wrapped around the drum when the second shaft 112 is rotated. The third puller wire 35 is sandwiched between the rim 120 and the arm 62 to minimize a risk of entanglement with other components inside the control handle. Notably, the through-bore 100 at the larger female end portion 86 is sized so that while the shafts 66 and 112 are axially aligned and thus share a common rotational axis they are not rotationally coupled to each other and thus are rotationally independent of each other. They function as radial sleeve bearing members.

Figure 14A:
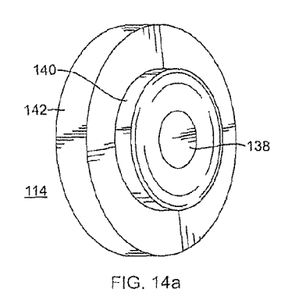
FIG. 14A is a perspective view of one side of an embodiment of a bearing of the actuation assembly.

The shaft body 116 on the other side of the rim 112 is inserted through the bearing 114 and a central partial bore in the second actuation dial 52. As illustrated in FIG. 14a, the bearing 114 has an smaller diameter annular disc portion 141 that sits in a through-hole 141 formed in the housing half 16b. The bearing 114 also as a larger diameter annular disc portion 142 that is adjacent the dial 52. It is understood that the bearing 114 can be integrally molded as part of the control handle housing half.

In communication with the central partial bore 136 of the dial 52 are two opposing radially transverse bores 150. A set screw 152 is inserted in each bore 150 for frictional contact with the shaft body 116 in rotationally coupling the dial 52 and the shaft 112.

Figure 14B:
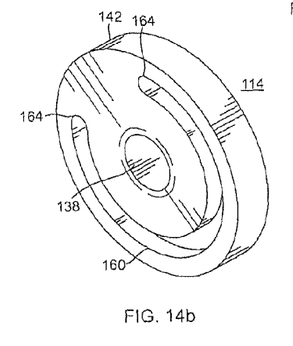
FIG. 14B is a perspective view of an opposite side of the bearing of FIG. 14A.

An off-center through-bore 156 parallel with the shaft 112 is formed in the actuation dial 52. The bore is in communication with a C-shaped groove 160 formed in the outer-facing surface of the larger diameter portion 142 of the bearing 114 (FIG. 14b). A press-fit pin 162 is inserted into the bore 156 with its end received and riding in the groove. Ends 164 of the groove act as stops for the pin 162 in limiting the degree of rotational movement of the dial 52 in setting a maximum and minimum travel of the third puller wire 35 for adjusting the distal assembly 17. It is understood that the groove and ends can be integrally molded as part of the control handle housing half.

A second locking cap screw 168 is received in the longitudinal partial bore 136 of the dial 52 and engages the second shaft 112 through a through bore 113 therein. The locking cap screw 168 secures the dial 52 to second shaft 112. The shaft 112 in turn secures the bearing 114 and housing half 16b to each other. As such, the shaft 112, the bearing 114 are maintained generally in the interior of the housing half 16b. When tightening the second locking screw 168, a screwdriver or a hex wrench can be inserted deeply into the longitudinal bore 100 of the rotational shaft (without the first locking cap screw 96 installed) and reach the bore 113 of the drum of the second shaft 112 to hold the shaft 112 stationary. The screwdriver or hex wrench engages a matching screw-driver receiving slot or a hexagonal cross section formed in the through-bore 100 at the drum 122. The first locking cap screw 96 can be installed and tightened while the deflection knob 50 (along with the shaft 66) is held stationary by the user.

The third puller wire actuation assembly 110 includes a second friction-inducing element, including a washer 170, e.g., a Belleville washer, to render the actuation dial 52 self-holding. In the illustrated embodiment, the washer is positioned on the second shaft 112 between the rim 120 and the bearing 114. The large contact surface area provided by the rim provides the friction torque for the dial 52 to be self holding. The washer is also compression preloaded under the second locking cap screw 168 and provides friction torque with the contact surfaces of the rim 120 and the bearing 114 to hold the dial 52 in the rotational position set by the user thus holding the adjustment of the distal assembly 17.

Figure 15A:
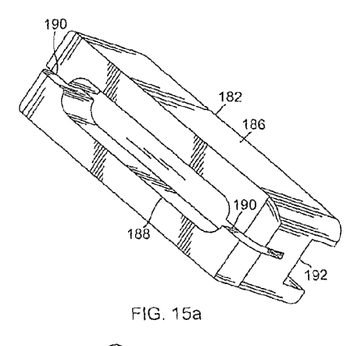
FIG. 15A is a perspective view of one side of an embodiment of a carriage.
Figure 15B:
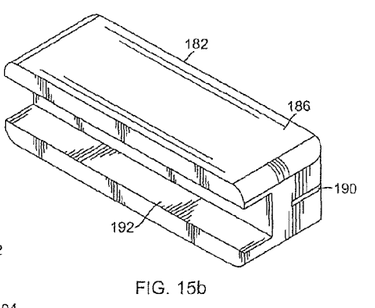
FIG. 15B is a perspective view of an opposite side of the carriage of FIG. 15A.

Because of the repeated cycles of bending the contraction wire 35 can experience around the drum 122, the contraction wire 35 within the control handle may comprise a tensile fiber segment which can better withstand stress and strain. To that end, a connector 180 (FIG. 9) is provided to connect a proximal end of the third puller wire 35a to a distal end of a tensile fiber segment 35b. As illustrated in FIGS. 15a and 15b, the connector 180 is received in a carrier 182 that translates along a central divider rib 184 (FIG. 7) formed in the housing handle 16a which also serves as a structural strengthening formation of the control handle. The carrier has a rectangular body 186 formed with a recess 188 in which the connector is nested. Two inlets 190 are formed in the body 186 to accommodate the third puller wire segment 35a at one end of the connector 180 and the tensile fiber 35b at the other end. An underside of the carrier body has an elongated slot 192 that engages the rib 184. The rib extends in the longitudinal direction between and generally parallel with the first and second puller wires 42.

In use, a suitable guiding sheath is inserted into the patient with its distal end positioned at a desired location. An example of a suitable guiding sheath for use in connection with the present invention is the Preface™ Braiding Guiding Sheath, commercially available from Biosense Webster, Inc. (Diamond Bar, Calif.). The distal end of the sheath is guided into one of the chamber, for example, the atria. A catheter in accordance with an embodiment of the present invention is fed through the guiding sheath until its distal end extends out of the distal end of the guiding sheath. As the catheter is fed through the guiding sheath, the distal assembly 17 is straightened to fit through the sheath. Once the distal end of the catheter is positioned at the desired location, the guiding sheath is pulled proximally, allowing the deflectable intermediate section 14 and distal assembly 17 to extend outside the sheath, and the distal assembly 17 returns to its original shape due to its shape-memory.

By manipulating and rotating the deflection knob 50 to deflect the intermediate section 14, the distal assembly 17 is then inserted into a pulmonary vein or other tubular region (such as the superior vena cava, or inferior vena cava) so that the outer circumference of the generally circular main region 39 of the assembly 17 is in contact with a circumference inside the tubular region. Turning the deflection knob 50 in one direction deflects the intermediate section 14 to that direction. Turning the deflection 50 in the opposite direction deflects the intermediate section 14 to that opposite direction. Preferably at least about 50%, more preferably at least about 70%, and still more preferably at least about 80% of the circumference of the generally circular main region is in contact with a circumference inside the tubular region.

The circular arrangement of the electrodes on the generally circular portion 39 permits measurement of the electrical activity at that circumference of the tubular structure so that ectopic beats between the electrodes can be identified. The size of the generally circular main region 39 permits measurement of electrical activity along a diameter of a pulmonary vein or other tubular structure of or near the heart because the circular main region has a diameter generally corresponding to that of a pulmonary vein or other tubular structure. By manipulating the dial 52, the generally circular main region 39, is adjusted to fit the pulmonary vein or other tubular structure. In the disclosed embodiment, by rotating the dial in one direction, the contraction wire 35 is drawn proximally to tighten and decrease the diameter of the generally circular region 39. By rotating the dial in the other direction, the contraction wire 35 is loosened to release the generally circular region 39 to its original diameter.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. For example, the catheter can be adapted such that the third puller wire advances and retracts another component such as a guide wire or a needle. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A control handle for a medical device having at least a first feature and a second feature subject to manipulation by a user, the medical device further having at least a first puller wire and a second puller wire for manipulating the first and second features, respectively, the control handle comprising:
    a housing with a first housing portion and a second housing portion;
    a first actuation assembly and a second actuation assembly being independently rotatable about a common rotational axis,
    the first actuation assembly comprising a first actuator, an arm rotatable about said common rotational axis, and a first shaft, the first actuator and the arm being rotationally coupled by the first shaft; the arm having at least one pulley, the first puller wire engaged with the at least one pulley;
    the second actuation assembly comprising a second actuator and a second shaft having a spool portion,
    wherein rotation of the first actuator rotates the arm in moving the at least one pulley to draw the first puller wire to manipulate the first feature of the medical device and wherein rotation of the second actuator wraps the second puller wire on the spool portion to manipulate the second feature of the medical device.

2. A control handle of claim 1, wherein the first shaft has a female end and the second shaft has a male end, and the male end is received in the female end such that the first and second shafts are axially aligned.

3. A control handle of claim 2, wherein the first and second shafts are rotationally independent.

4. A control handle of claim 1, wherein the first actuation assembly includes a first friction-inducing compression device to maintain rotational position of the first actuator.

5. A control handle of claim 1, wherein the second actuation assembly includes a second friction-inducing compression device to maintain rotational position of the second actuator.

6. A control handle of claim 4, wherein the first actuation assembly includes a first screw to adjust a compression force of the first friction-inducing compression device.

7. A control handle of claim 5, wherein the second actuation assembly includes a second screw to adjust a compression force of the second friction-inducing compression device.

8. A control handle of claim 1, wherein the second actuation assembly further includes a stop to limit range of rotation of the second actuator.

9. A control handle of claim 8, wherein the second actuation assembly includes a bearing generally situated between the spool portion and the second actuator.

10. A control handle of claim 9, wherein the bearing is configured with a groove and a pin projecting from the second actuator rides in the groove.

11. A control handle of claim 1, wherein the control handle has a longitudinal axis that is generally perpendicular to the common rotational axis.

12. A control handle of claim 1, wherein the medical device includes another puller wire and the first actuation assembly includes at least two pulleys, each of the at least two pulleys being engaged with a respective puller wire for bidirectional deflection of the medical device.

* * * * *